United States Patent
Weisshaupt et al.

(10) Patent No.: US 11,369,395 B2
(45) Date of Patent: Jun. 28, 2022

(54) SURGICAL CLAMP PRODUCED BY ADDITIVE MANUFACTURING AND A METHOD FOR PRODUCING SUCH A CLAMP

(71) Applicant: AESCULAP AG, Tuttlingen (DE)

(72) Inventors: Dieter Weisshaupt, Immendingen (DE); Tobias Koller, Tuttlingen (DE)

(73) Assignee: AESCULAP AG, Tuttlingen (DE)

( * ) Notice: Subject to any disclaimer, the term of this patent is extended or adjusted under 35 U.S.C. 154(b) by 348 days.

(21) Appl. No.: 16/493,489

(22) PCT Filed: Mar. 12, 2018

(86) PCT No.: PCT/EP2018/056116
§ 371 (c)(1),
(2) Date: Sep. 12, 2019

(87) PCT Pub. No.: WO2018/166989
PCT Pub. Date: Sep. 20, 2018

(65) Prior Publication Data
US 2020/0383695 A1    Dec. 10, 2020

(30) Foreign Application Priority Data
Mar. 16, 2017   (DE) .......................... 102017105706.4

(51) Int. Cl.
*A61B 17/00*    (2006.01)
*A61B 17/28*    (2006.01)
(Continued)

(52) U.S. Cl.
CPC .......... *A61B 17/2816* (2013.01); *B22F 10/20* (2021.01); *B28B 1/001* (2013.01);
(Continued)

(58) Field of Classification Search
CPC .................. A61B 17/2816; A61B 2017/00526
See application file for complete search history.

(56) References Cited

U.S. PATENT DOCUMENTS 2,305,156 A * 12/1942 Grubel ............... A61B 17/2816
                                                     403/114
3,952,749 A *  4/1976 Fridolph ............ A61B 17/2816
                                                     606/208
(Continued)

FOREIGN PATENT DOCUMENTS

DE        8316305 U1    9/1983
DE    202011000800 U1   5/2011
(Continued)

OTHER PUBLICATIONS

Scissor Snake Family. Thingiverse Website [Online], Submitted by user ricswika, Nov. 18, 2016 [retrieved Nov. 16, 2021], Retrieved from the Internet: <URL: https://www.thingiverse.com/thing:1902131>. (Year: 2016).*
(Continued)

Primary Examiner — Jacob J Cigna
(74) Attorney, Agent, or Firm — Culhane Meadows PLLC; Christopher A. Rothe (57) ABSTRACT

A medical instrument includes at least a first instrument shank and a second instrument shank that can be moved in relation to each other. The first instrument shank is a male instrument shank with a male bearing section. The second instrument shank is a female instrument shank with a female bearing section that includes a through-opening. The first instrument shank is arranged on the second instrument shank by the male bearing section engaging through the through-opening of the female bearing section. The instrument is produced by an additive manufacturing method.

15 Claims, 4 Drawing Sheets

(51) Int. Cl.
- *A61B 90/00* (2016.01)
- *B28B 1/00* (2006.01)
- *B33Y 10/00* (2015.01)
- *B33Y 80/00* (2015.01)
- *B22F 10/20* (2021.01)

(52) U.S. Cl.
CPC .............. *B33Y 10/00* (2014.12); *B33Y 80/00* (2014.12); *A61B 2017/00526* (2013.01); *A61B 2090/0813* (2016.02)

(56) References Cited

U.S. PATENT DOCUMENTS

| | | | | |
|---|---|---|---|---|
| 8,241,228 | B1* | 8/2012 | Cohen | A61B 17/3201 600/573 |
| 9,301,846 | B2* | 4/2016 | Landon | A61F 2/389 |
| 10,925,626 | B2* | 2/2021 | Barthelmes | A61B 17/2816 |
| 2011/0311389 | A1* | 12/2011 | Ryan | B22F 3/15 419/27 |
| 2014/0140788 | A1* | 5/2014 | Frodis, III | F16B 33/02 411/366.1 |
| 2014/0373689 | A1* | 12/2014 | Sildve | B25B 7/02 81/416 |
| 2015/0057702 | A1 | 2/2015 | Edmondson et al. | |
| 2016/0000481 | A1 | 1/2016 | Ehmke et al. | |
| 2016/0008041 | A1 | 1/2016 | Makhlouf | |
| 2017/0020571 | A1 | 1/2017 | Hawkes et al. | |
| 2017/0196578 | A1 | 7/2017 | Zubrod | |

FOREIGN PATENT DOCUMENTS

| | | |
|---|---|---|
| DE | 202013010321 U1 | 1/2014 |
| DE | 102016200131 A1 | 4/2016 |
| EP | 2873381 A1 | 5/2015 |
| WO | 2012021779 A2 | 2/2012 |

OTHER PUBLICATIONS

Cummins et al., "The Rise of Additive Manufacturing", 2010, retrieved from the internet:https://www.theengineer.co.uk/issues/24-may-2010/the-rise-of-additive-manufacturing, 11 pages.

German Search Report for German Application No. 10 2017 105 706.4, dated Dec. 27, 2017 with translation, 17 pages.

International Search Report and Written Opinion for International Application No. PCT/EP2018/056116, dated Jun. 4, 2018, 9 pages.

Office Action received in Japanese Application No. 2019-550745 dated Apr. 13, 2022, with translation, 13 pages.

* cited by examiner

Fig. 9

SURGICAL CLAMP PRODUCED BY ADDITIVE MANUFACTURING AND A METHOD FOR PRODUCING SUCH A CLAMP

CROSS REFERENCE TO RELATED APPLICATIONS

This application is the national phase entry of International Application No. PCT/EP2018/056116, filed Mar. 12, 2018, which claims the benefit of priority of German Application No. 10 2017 105 706.4, filed Mar. 16, 2017. The contents of International Application No. PCT/EP2018/056116 and German Application No. 10 2017 105 706.4 are incorporated by reference herein in their entireties.

FIELD

The invention relates to a medical instrument comprising at least a first instrument branch and a second instrument branch which are movable relative to each other, wherein the first instrument branch is formed as a male instrument branch with a male bearing portion, and the second instrument branch is formed as a female instrument branch with a female bearing portion having a through opening, wherein the first instrument branch is arranged on the second instrument branch in that the male bearing portion penetrates the through opening of the female bearing portion. It furthermore relates to a method of manufacturing a medical instrument by means of an additive manufacturing method.

BACKGROUND

The manufacture of a conventional surgical instrument with box lock is relatively complex in a disadvantageous way. Such instruments with box lock include, for example, scissors, clamps, forceps or similar instruments that have two instrument branches/instrument parts that can be positioned relative to each other, in particular by pivoting. The two instrument branches are designed and mounted in such a way that one of them penetrates the other, it can also be said that one branch is inserted through the box of the other, thus bearing the name "box lock". Usually, the two instrument branches are prefabricated separately, for example by deformation and/or machining. The branches prefabricated in this way are then inserted into each other and pressed by expanding a closure region of the female instrument branch. Further working steps may be necessary, such as drilling, grinding, levelling, hardening and/or brushing.

It is a disadvantage in the manufacture of such known instruments that, as a rule, a great deal of time and effort with numerous operations is required. This results in cost-intensive and tool-intensive manufacturing, in that hardly any automation possibilities exist and in that even a high manual effort may be necessary. Another disadvantage of known medical instruments with box lock is that their branches that are relatively movable to each other are usually coupled to each other via a (pivot) axis. Therefore, there is always an area between the branches that is difficult to access for cleaning or disinfecting purposes because, apart from the aforementioned rotation to each other, there are no other possibilities for relative positioning.

SUMMARY

The object underlying the invention with respect to this prior art is to provide a medical instrument that is not subject to the problems of the prior art described above in terms of manufacturing engineering. In particular, its manufacture is to be cost-effective, have a high degree of automation and preferably enable (largely) tool-free assembly. Furthermore, the instrument is to be improved with regard to its suitability for cleaning and sterilization as compared to the prior art.

This object is solved according to the invention by a medical instrument having at least a first instrument branch/instrument part and a second instrument branch/instrument part, which are relatively movable to each other. The first instrument branch is designed as a male instrument branch with a male bearing portion. The second instrument branch is designed as a female instrument branch with a female bearing portion having a through opening (push-through box). The first instrument branch is arranged at the second instrument branch in that the male bearing portion penetrates the through opening (push-through box) of the female bearing portion. The instrument according to the invention is characterized by the fact that it (at least the first instrument branch) is manufactured using an additive manufacturing method.

With regard to a method, the object is solved by the method of manufacturing a medical instrument, in particular an instrument according to the invention, by means of an additive manufacturing method, according to which at least a first, male instrument branch/instrument part with a male bearing portion and a second instrument branch/instrument part as female instrument branch with a female bearing portion (push-through box) having a through opening are formed, wherein at least the male bearing portion is manufactured additively (according to the generally known generative/additive manufacturing method) so as to penetrate the through opening of the female bearing portion.

The manufacture of two instrument branches inserted into each other by means of an additive manufacturing method is successful because, for example, in a certain opened position of the instrument, the distance between the two instrument branches is such that the branches do not merge during manufacture and can subsequently be moved/pivoted relative to each other. According to the invention, the branches are manufactured in such a way that they are produced separately from each other in a single manufacturing step. This means that both branches are produced simultaneously, whereby they are built up additively or generatively directly in their intended arrangement to each other and constellation, i.e. with a box lock. It can also be said that, in contrast to the prior art, where the two branches are first produced separately from each other and are subsequently assembled with each other, according to the invention the two branches are coupled with each other during their production in the desired manner, in particular are coupled/interlocked so that they can be positioned relative to each other in the intended manner. In an advantageous way, the previously necessary, tool-intensive final assembly step (interlocking) of the two branches is no longer required. A further advantage is that the invention can significantly reduce the number of required manufacturing steps as compared to current manufacturing methods, which saves time and costs. However, the instrument can still be hardened, drilled, riveted and/or surface-treated after additive manufacturing, depending on the respective requirements. The invention covers almost all types of surgical instruments with box lock, e.g. forceps, clamps, scissors, etc.

The instrument according to the invention preferably has a closure region in which the two branches of the instrument are connected or coupled. This closure region/coupling region/connection region is formed by the male bearing portion (which can also be referred to as coupling portion, connection portion or closure portion) of the first branch and the female bearing portion/push-through box (which can also be referred to as coupling portion, connection portion or closure portion) of the second branch. The male portion is accommodated in or penetrates through the through opening of the female portion.

A preferred embodiment of the invention provides that the female bearing portion completely surrounds or encloses the through opening. This enables a particularly stable and precise guidance of the two branches to each other.

A further preferred embodiment provides that there is play between the male bearing portion of the first instrument branch and the female bearing portion of the second instrument branch in a relative position of the first instrument branch to the second instrument branch, which can also be referred to as manufacturing position, since the instrument is manufactured in this position, in such a way that the first instrument branch and the second instrument branch can be arranged without contact to each other/into each other. In particular, the bearing portions of both instrument parts can each have three individual partial areas: a central bearing region or closure region, in which the two instrument branches overlap each other in every position (functional position and manufacturing position), and lateral bearing regions or closure regions adjacent on both sides, in which the two branches overlap each other only if they are in a different angular position (functional position) to each other than in the manufacturing position, for example in the closed state of the instrument. Mutual contact between the two branches within the framework of additive manufacturing can be prevented particularly easily, if, according to a preferred embodiment, the area of the male bearing portion covered by the female bearing portion in the manufacturing position has a height which is lower than the clear width of the through opening. In particular, the two instrument parts can be designed in such a way that in a certain opening position (manufacturing position), for example between 80° and 120°, they are spaced apart in the entire closure region and do not contact or touch each other. This can be achieved, for example, by making the central closure region of the male instrument part and/or the central closure region of the female instrument part thinner than the respective lateral closure regions. In this way, the central closure regions of the two instrument parts do not touch each other in any position, so that a material connection of the two instrument parts during production is avoided. While the lateral closure regions overlap and even touch each other (directly or indirectly, for example, with contact structures or contact elements described in more detail below) when the instrument is closed to a certain degree (functional position), they do not overlap in the manufacturing position/state, so that they also cannot touch each other.

According to a preferred embodiment, there is an angle of approx. 80° to approx. 120°, preferably of approx. 85° to approx. 115°, and particularly preferably of approx. 90° to approx. 110° between the first instrument branch and the second instrument branch in the manufacturing position. Preferably, the instrument branches in the manufacturing position are at such an angle or in such a position relative to each other that does not occur or only occurs with a low probability when the instrument is used as intended in practice. This makes it particularly easy to ensure that the instrument functions safely (good pivoting guidance in the functional position(s)).

An advantageous embodiment of the invention provides that contact structures are formed on the first instrument branch and/or on the second instrument branch. These serve to establish mutual contact between the first instrument branch and the second instrument branch in a function/usage position that deviates from the manufacturing position. In this way, a defined, secure and stable guidance of the branches to each other and against each other can be achieved during practical use, despite the spatial separation of the branches from each other caused by the manufacturing. According to an embodiment, the male branch has at least one contact structure in the closure region or in the male bearing portion in the form of an elevation or a small bench, which reduces the play in the instrument closure when the instrument is closed. Preferably, two such small benches or elevations are formed or arranged on each side. According to the invention, a particularly effective play compensation with simultaneous easy actuation can be achieved by forming resilient tongues in the area of the elevation or the small bench. Thus, a spring force is applied between the branches, the strength of which determines the actuating force and guidance of the instrument. In the case of an embodiment described in the following having a plug, it is practical for the branches to be arranged and fastened relative to one another by means of a separate axis element, which passes through corresponding recesses in the branches, in order to define a clear movement of the two parts relative to one another.

The first instrument branch and the second instrument branch can be positioned pivotably to each other by means of a push-through axis. As a rule, such a push-through axis can be designed as a rivet.

Alternatively, one of the instrument branches can have a guiding projection rising in the direction of the other instrument branch, which engages in a corresponding circular arc-shaped recess on the other instrument branch for the pivotable positioning of the instrument branches (motion-link guidance). In particular, the recess can be formed on the female bearing portion, in particular on both sides. The guiding projection can be formed on the male bearing portion, in particular on both sides.

It is of particular advantage that such an embodiment does not require an axis, push-through axis or a rivet. On the one hand, this results in the instrument having one component less, so that at least one working step is omitted in its manufacture as compared to an instrument with push-through axis. Another essential and important advantage is that the instrument can be manufactured with a defined closing force/opening force/actuating force. This is due to the fact that the interaction of the male and female branches, in particular the forces acting between them as a result of their mutual fit, can be produced in a defined way, which can only be achieved with difficulty with an instrument with a riveted through axis. In the riveting process, the two sides of the closure box of the male branch are usually deformed, in particular compressed. In a disadvantageous way, the degree of such a deformation cannot or can only be influenced with difficulty in a defined way, so that a riveting process can only poorly be validated for a certain force (closing force, opening force, actuating force). In practice, this problem ranges that far that when several riveting machines are used in production, each machine produces instruments with a different movement, even though both the machines and their parameters are identical. This results in instruments that differ significantly from each other in the movement (actuating force), which can only be corrected by extensive reworking to such an extent that an approximately identical closing force, i.e. an approximately identical movement, can be achieved. It is a great advantage that the above problems can be avoided with an embodiment with a motion-link guidance. The projections and grooves, in particular circular arc-shaped projections and corresponding circular arc-shaped grooves can be formed in particular during additive manufacturing, in particular during a laser sintering process, in particular on the opposite surfaces of the lateral closure regions or bearing portions of the male and female instrument parts. These are arranged concentrically to the intended center of rotation of the two instrument branches. It is particularly advantageous if the grooves and projections are also provided with approach chamfers, so that the respective projection can be inserted funnel-like into the associated groove when the two branches are moved from the manufacturing position to the usage position. Due to the concentricity of the grooves and projections, there is no need for an axis as a separate component and manufacturing steps can be omitted. The projections can be in the form of continuous circular arcs or in the form of a projection or several individual projections arranged on a corresponding circular arc. One embodiment is characterized in that grooves and/or projections are provided with a friction-reducing layer. Alternatively, they can be made of a suitable material, such as PEEK, PE, etc., and can be mounted on the lateral closure portions. In addition, oblique surfaces may be provided at the lateral ends of the circular arc-shaped groove and/or at the corresponding projection. These form a kind of entry funnel, which facilitates the entry of the projection into the groove. The oblique surfaces can also be designed in such a way that the real closure (i.e. there is no more wobbling between the two parts) is only formed shortly before the instrument is in the closed position.

According to a preferred embodiment, the instrument has an inhibition structure. This serves to ensure that the instrument cannot be moved from one of its functional/usage positions to the manufacturing position easily or accidentally during use. The inhibition structure is therefore designed in such a way that, when the instrument is transferred from a usage position to the manufacturing position, the relative movement of both instrument branches is inhibited (resistance to movement/threshold), which must be overcome by an increased actuating force by the user. It can also be said that in this way a surmountable stop is formed for an opening movement of the instrument. This has the advantage that the instrument does not open beyond a certain point during regular use and it is thus prevented that it is accidentally transferred to the manufacturing position. However, it is easily possible to bring the instrument into the manufacturing position by exerting an actuating force which overcomes the inhibition. In the manufacturing position, the instrument branches (within limits) can be moved and/or rotated in several directions to each other, thus facilitating easy and effective cleaning, maintenance and disinfection. At the same time, it is ensured that the manufacturing position is not accidentally reached during regular use of the instrument. The inhibition or the surmountable stop can, for example, be achieved by forming different groove depths. Alternatively, it can be achieved by placing recesses and projections in such a way that they can be selectively brought into engagement with each other, i.e. depending on the opening angle of the branches. For example, several concentric corresponding grooves and projections can be provided. In the case that the virtual pivot axis is formed by means of grooves and projections, the remaining areas of the lateral closure surfaces can only partially or not at all touch each other.

The branches can in particular consist of/be made of metal and/or ceramics.

According to a preferred embodiment, a recess can be formed in at least one of the branches, in particular in at least one of the bearing portions. A plug can be or will be pressed into this, which determines the movement or the actuating force of the instrument. The plug may be made of a different material than the instrument parts, for example a plastic material such as PEEK, PE, PA or another metallic material such as austenitic steel.

The (lateral) distance between the two central closure regions/bearing portions depends on the manufacturing accuracy of the machinery used for additive manufacturing. This distance is preferably between 0.05 mm and 0.3 mm. The two instrument parts can be constructed in such a way that they are already inserted into each other in a 3D CAD model. This 3D CAD model can be the basis for a machine used for additive manufacturing, for example a laser sintering machine.

It can be said that the invention makes it possible for the first time to manufacture surgical instruments using an additive or generative manufacturing method without the instrument parts or instrument branches connecting with each other in a box lock, in particular connecting or merging with each other in a material-locking manner. The entire instrument is manufactured using a generative or additive manufacturing method. The invention relates both to a manufacturing method for such instruments as well as to the instruments themselves with an appropriately formed box lock.

BRIEF DESCRIPTION OF THE DRAWING FIGURES

The invention is explained in more detail below using drawings as examples. These show.

The drawings are only schematic in nature and serve only to understand the invention.

DETAILED DESCRIPTION

Figure 1:
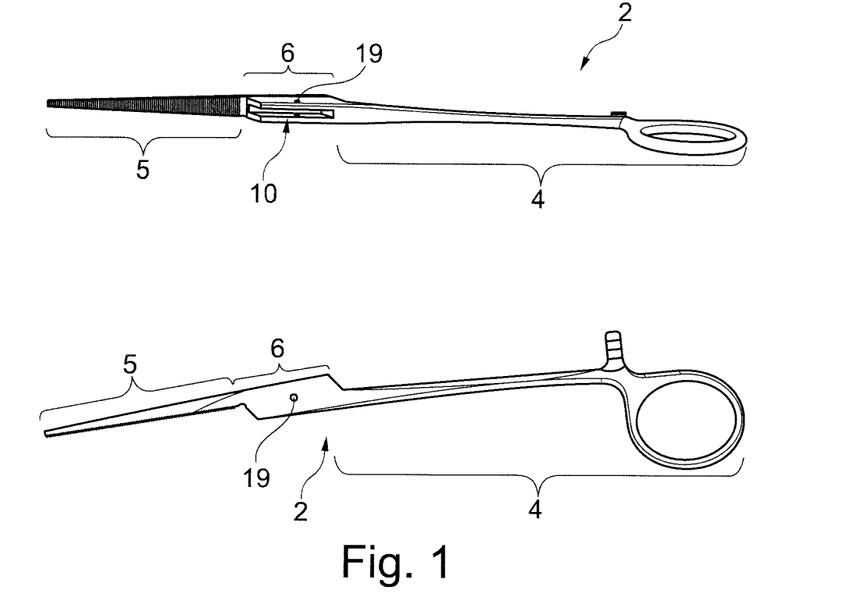
FIG. 1 shows a female instrument branch in two different perspective views.
Figure 2:
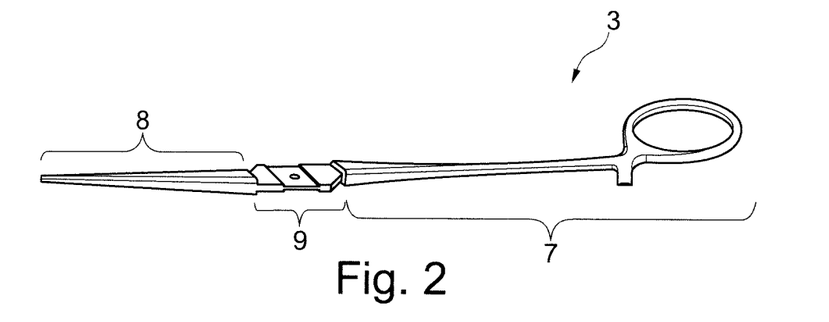
FIG. 2 shows a male instrument branch in a perspective view.

FIGS. 1 and 2 show, as an example of an instrument 1 according to the invention, a surgical clamp 1. FIG. 1 shows its female branch 2, while FIG. 2 shows its male branch 3. The female branch 2 has a handle portion 4, a clamping portion 5 and a female bearing portion (push-through box) 6 arranged between them. Similarly, the male branch 3 has a handle portion 7, a clamping portion 8 and a male bearing portion 9 arranged between them. The female bearing portion 6 has a push-through/through opening 10. It is expressly pointed out that FIGS. 1 and 2 are only presented for the sake of presenting and explaining the two branches 2, 3 more clearly, but that the clamp 1 according to the invention, which is produced using an additive or generative manufacturing method according to the invention, cannot be disassembled/assembled, i.e. the two branches 2, 3 cannot be separated from each other without being destroyed.

Figure 3:
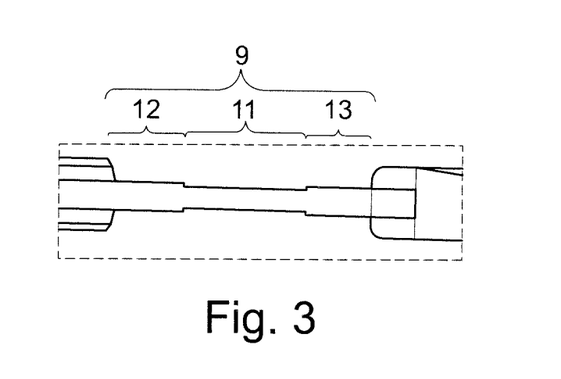
FIG. 3 shows an enlarged detail of the male instrument branch in the area of the bearing portion.

FIG. 3 shows the male bearing portion 9 enlarged in a side view. It is shown that the male bearing portion 9 has three individual parts: a central bearing region or closure region 11, in which the two instrument branches 2, 3 overlap each other in every relative position, and lateral bearing regions or closure regions 12 or 13 adjacent on both sides, in which the two branches 2, 3 overlap only if they are in a different angular position to each other than in the manufacturing position (shown in FIG. 4), for example in the closed state of the instrument 1. The central male bearing portion 11 has a height h which is smaller than the height H of the through opening 10 of the female bearing portion, see in particular FIG. 5. As a result of this formation, there is a (double) gap in the manufacturing position between the male branch 3 and the female branch 2 with a respective gap height of, for example, 0.05 mm to 0.3 mm and thus there is no contact. The two branches 2, 3 can therefore be produced in the manufacturing position by means of an additive or generative method, such as laser sintering, without being connected or baked together, so that a relative mobility of the branches 2, 3 to each other is ensured.

Figure 6:
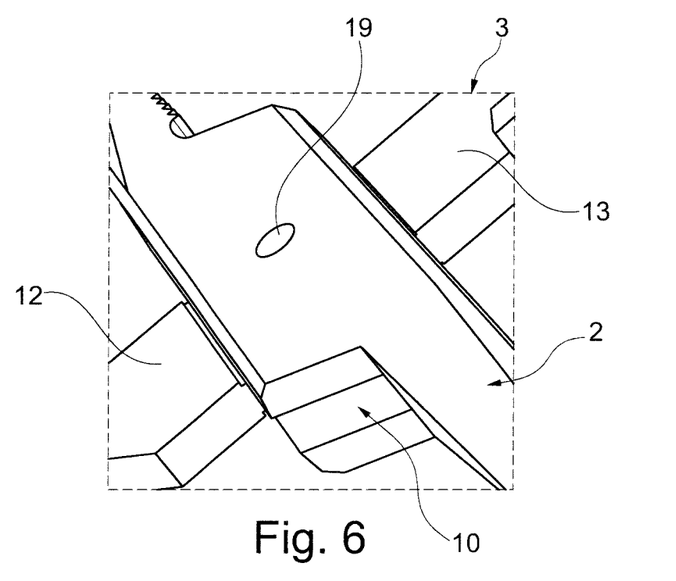
FIG. 6 shows the area of both bearing portions in the manufacturing position in a perspective view.

In order to achieve a desired mutual guidance of the branches 2, 3 when using the instrument 1, the lateral bearing or closure regions 12, 13 are formed according to the embodiment shown in FIG. 6 with height h' which is increased as compared to the central bearing portion 11. The height h' essentially corresponds to the height H of the through opening 9, so that the two branches 2, 3 support each other in a position deviating from the manufacturing position, i.e. in a usage position, and thus achieve the desired guidance.

Figure 4:
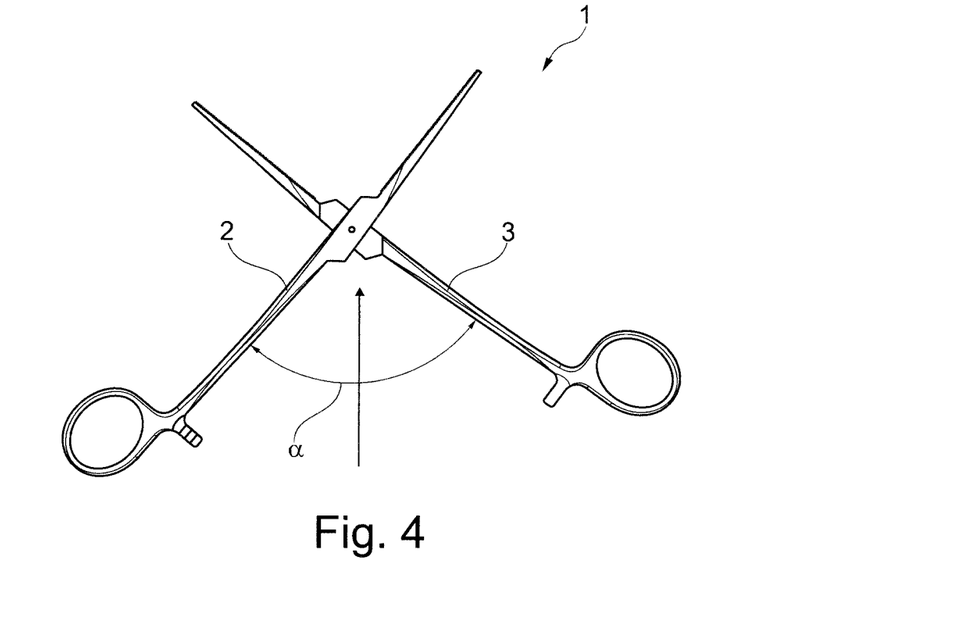
FIG. 4 shows an instrument in a manufacturing position in a top view.
Figure 5:
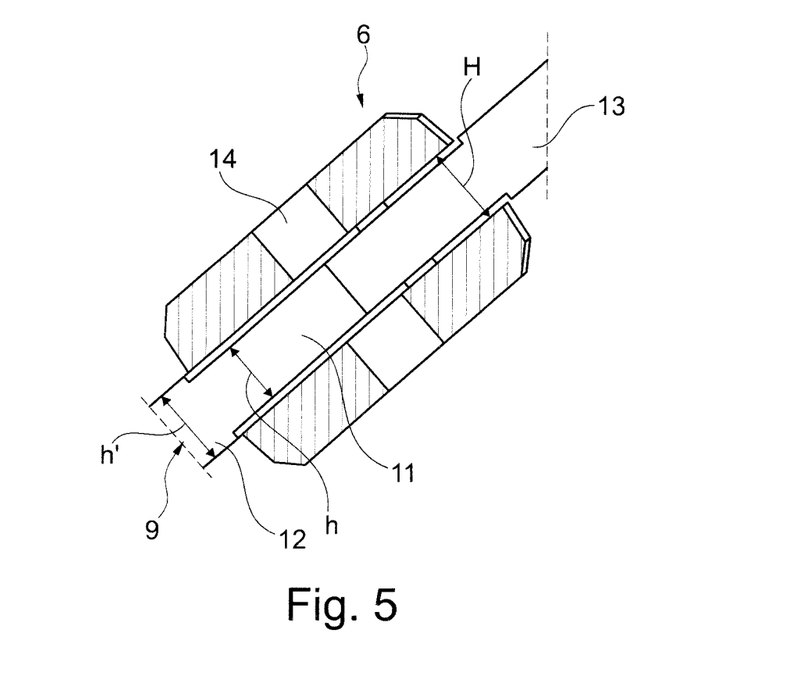
FIG. 5 shows the area of both bearing portions in the manufacturing position enlarged and in a sectional view.

It is noted that the additive manufacturing of the instrument 1 takes place in the manufacturing position shown in FIG. 4, whereby the two branches 2, 3 are built up additively in the inserted state. This means that the branches 2, 3 are not manufactured individually and are then connected to each other/inserted, but that their additive build-up occurs simultaneously with the desired box lock. FIG. 4 shows a manufacturing position in which the angle α between branches 2, 3 is about 90°.

Figure 7:
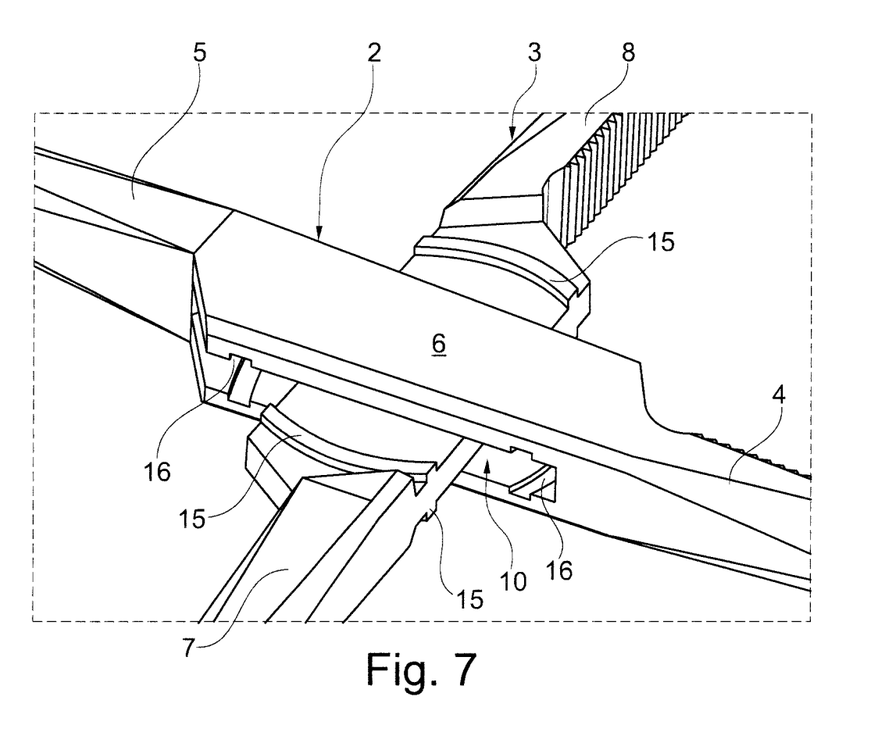
FIG. 7 shows the area of both bearing portions of an embodiment in the manufacturing position in a perspective view.

While the two branches 2, 3 of the embodiment of FIG. 6 are pivotably connected to each other with a push-through axis 14, which is inserted through corresponding axis holes 19 in the branches 2, 3, FIG. 7 shows an embodiment deviating from this without such an axis. The male bearing portion 9 is provided on both sides with two essentially circular arc-shaped elevations 15. The female bearing portion 6 is correspondingly provided with circular arc-shaped recesses 16 on both sides of the through opening 10. The elevations 15 and the recesses 16 are designed to be engaged with each other in such a way that they form a guiding structure or guideway by means of which the two branches 2, 3 are guided relative to each other in the functional position region when pivoted. If the branches 2, 3 are not in a functional position but in the manufacturing position, the recesses 16 and the elevations 15 are not engaged so that there is no contact between branches 2, 3.

Figure 8:
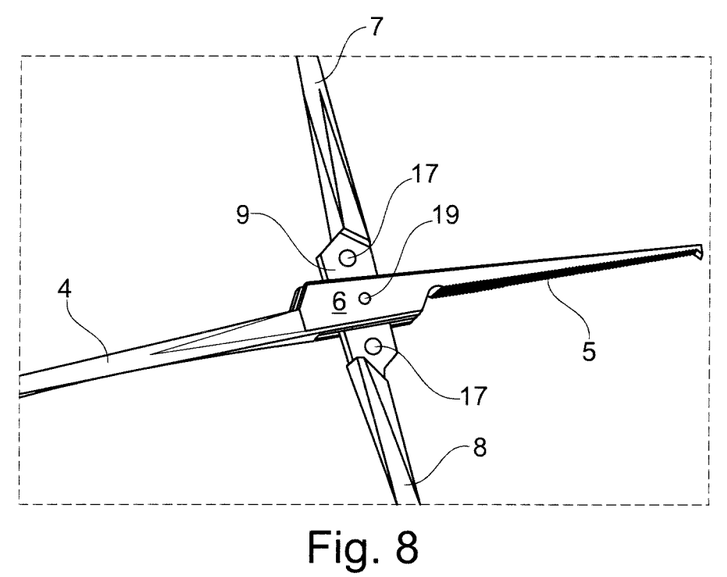
FIG. 8 shows the area of both bearing portions of an embodiment in the manufacturing position in a perspective view.

FIG. 8 shows an embodiment of the instrument 1, in which contact structures are formed at the male bearing portion 9 in the form of plugs 17 preferably inserted or pressed into recesses (can be glued on in the form of nubs). The plugs 17 are designed to determine the movement or actuating force of the instrument 1 and may be made of a different material than the instrument parts, e.g. a plastic such as PEEK, PE, PA or another metallic material such as austenitic steel.

Figure 9:
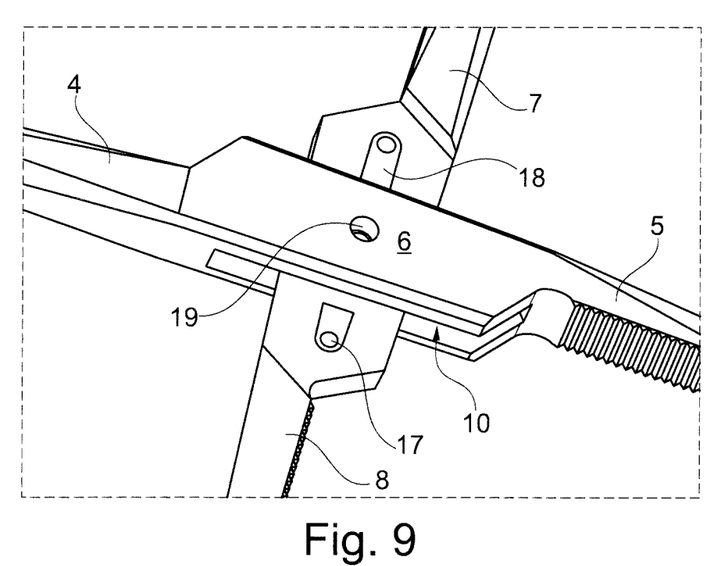
FIG. 9 shows the area of both bearing portions of an embodiment in the manufacturing position in a perspective view.

FIG. 9 shows a further embodiment in which the contact structures are formed in the form of resilient tongues 18, at the free ends of which plugs or nubs 17 can preferably be arranged according to FIG. 8.

It is also noted that the embodiment without bearing axis according to FIG. 7 can be combined with the contact structures according to FIG. 8 or 9. Also for the embodiment without axis according to FIG. 7, a bearing area formed according to FIG. 3 can be used advantageously.

The invention claimed is:

1. A medical instrument comprising at least a first instrument branch and a second instrument branch which are pivotable relative to each other, wherein the first instrument branch is formed as a male instrument branch with a male bearing portion, and the second instrument branch is formed as a female instrument branch with a female bearing portion having a through opening, wherein the first instrument branch is arranged on the second instrument branch in that the male bearing portion penetrates the through opening of the female bearing portion, wherein the instrument is manufactured by an additive manufacturing method, wherein one of the first and second instrument branches has a guiding projection that projects toward the other of the first and second instrument branches, the guiding projection engaging a corresponding circular arc-shaped recess in said other of the first and second instrument branches to form a guiding structure during pivoting of the instrument branches relative to each other, wherein the guiding projection and the recess are arranged concentrically to a center of rotation of the first instrument branch and the second instrument branch.

2. The medical instrument according to claim 1, wherein the female bearing portion completely surrounds the through opening.

3. The medical instrument according to claim 1, wherein there is play between the male bearing portion of the first instrument branch and the female bearing portion of the second instrument branch in a relative position of the first instrument branch to the second instrument branch, in such a way that the first instrument branch and the second instrument branch are arranged without contact to each other.

4. The medical instrument according to claim 1, wherein the first instrument branch and the second instrument branch can be positioned pivotably to each other by a push-through axis.

5. The medical instrument according to claim 1, wherein the recess is formed on the female bearing portion, and the guiding projection is formed on the male bearing portion.

6. The medical instrument according to claim 1, wherein the guiding projection and the recess are provided with oblique surfaces at lateral ends thereof forming an entry funnel.

7. The medical instrument according to claim 1, wherein the guiding projection and/or the recess are provided with a friction-reducing layer.

8. A method of manufacturing a medical instrument by an additive manufacturing method comprising the steps of:

forming at least a first instrument branch as a male instrument branch with a male bearing portion; and forming a second instrument branch as a female instrument branch with a female bearing portion having a through opening, wherein the male bearing portion is manufactured additively in a manufacturing position, in which the male bearing portion penetrates the through opening of the female bearing portion, and wherein the male bearing portion and the female bearing portion each have a central bearing portion and a lateral bearing portion, in which the first instrument branch and the second instrument branch overlap each other in a functional position and a manufacturing position, and lateral bearing portions adjacent on both sides, in which the first and second instrument branches overlap each other only in the functional position.

9. The method according to claim 8, wherein the instrument is manufactured by laser sintering.

10. The method according to claim 8, wherein a gap of approximately 0.3 mm to 0.5 mm is produced between the first instrument branch and the second instrument branch.

11. The method according to claim 8, wherein an area of the male bearing portion covered by the female bearing portion in the manufacturing position has a height which is lower than the through opening.

12. The method according to claim 8, wherein there is an angle α of approximately 80° to approximately 120° between the first instrument branch and the second instrument branch in the manufacturing position.

13. The method according to claim 8, wherein lateral bearing portions, at least one plug and/or at least one spring tongue are formed as contact structures on the first instrument branch and/or on the second instrument branch to establish mutual contact between the first instrument branch and the second instrument branch in a usage position that deviates from the manufacturing position.

14. The method according to claim 13, wherein the contact structures comprise at least one plug made from a different material than the instrument branches.

15. The method according to claim 14, wherein the instrument branches are made from metal and/or ceramics and the at least one plug is made from one of PEEK, PE, PA or austenitic steel.

* * * * *